(12) United States Patent
Baecklund

(10) Patent No.: US 10,549,126 B2
(45) Date of Patent: Feb. 4, 2020

(54) POSITION DETECTOR

(71) Applicant: ScandiDos AB, Uppsala (SE)

(72) Inventor: Per Baecklund, Uppsala (SE)

(73) Assignee: SCANDIDOS AB (SE)

( * ) Notice: Subject to any disclaimer, the term of this patent is extended or adjusted under 35 U.S.C. 154(b) by 530 days.

(21) Appl. No.: 15/506,673

(22) PCT Filed: Jun. 26, 2015

(86) PCT No.: PCT/EP2015/064489
§ 371 (c)(1),
(2) Date: Feb. 24, 2017

(87) PCT Pub. No.: WO2016/030046
PCT Pub. Date: Mar. 3, 2016

(65) Prior Publication Data
US 2017/0274225 A1   Sep. 28, 2017

(30) Foreign Application Priority Data

Aug. 27, 2014   (EP) ..................................... 14182525

(51) Int. Cl.
*A61N 5/00* (2006.01)
*A61N 5/10* (2006.01)

(52) U.S. Cl.
CPC ......... *A61N 5/1082* (2013.01); *A61N 5/1042* (2013.01); *A61N 5/1065* (2013.01); *A61N 5/1075* (2013.01)

(58) Field of Classification Search
CPC .. A61N 5/1042; A61N 5/1048; A61N 5/1065; A61N 5/1075; A61N 5/1082
See application file for complete search history.

(56) References Cited

U.S. PATENT DOCUMENTS

| | | | |
|---|---|---|---|
| 6,134,296 A | 10/2000 | Siochi | |
| 2006/0122502 A1 | 6/2006 | Scherch et al. | |
| 2017/0023696 A1* | 1/2017 | Morton | ................ G01N 23/203 |

FOREIGN PATENT DOCUMENTS

| | | |
|---|---|---|
| CN | 101247850 A | 8/2008 |
| CN | 103776375 A | 5/2014 |
| EP | 2 489 310 A1 | 8/2012 |
| WO | WO 2011/098891 A1 | 8/2011 |
| WO | WO 2014/077767 A1 | 5/2014 |

\* cited by examiner

*Primary Examiner* — Dani Fox
(74) *Attorney, Agent, or Firm* — Condo Roccia Koptiw LLP

(57) ABSTRACT

A position detector arranged to be mounted at a radiation detector of a radiotherapy treatment apparatus, which includes a gantry rotatable about a gantry rotation axis, and a collimator rotatable about a collimator rotation axis. The radiation detector is mounted at the collimator. The position detector comprises: —an accelerometer device, which is arranged to detect at least gravitational acceleration in at least one dimension; —a gyro device arranged to detect at least angular velocity in at least one dimension; wherein the accelerometer device and the gyro device in common are arranged to be operative in three dimensions, and —a controller connected with the accelerometer and the gyro; wherein the controller is arranged to receive first input data from the accelerometer device and second input data from the gyro device, and to determine at least a collimator angle and a gantry angle by means of the first and second input data.

20 Claims, 4 Drawing Sheets

POSITION DETECTOR

CROSS REFERENCE TO RELATED APPLICATIONS

This application is the National Stage Entry under 35 U.S.C. § 371 of Patent Cooperation Treaty Application No. PCT/EP2015/064489, filed 26 Jun. 2015, which claims the benefit of European Patent Application No. 14182525.7, filed 27 Aug. 2014, the contents of which are hereby incorporated by reference herein.

FIELD OF THE INVENTION

The present invention relates to a position detector for a radiation therapy treatment apparatus, which includes a gantry rotatable about a gantry rotation axis, and a collimator rotatable about a collimator rotation axis.

BACKGROUND OF THE INVENTION

A radiation therapy treatment apparatus is typically used for treatment of cancer in the human body. The technology has been developed towards an increased precision in where the radiation dose is delivered. The goal is to be able to treat only the tumor cells and not the surrounding healthy tissue, in order to limit the negative effects on the healthy tissue subjected to radiation. Before the treatment is actually carried out, a treatment plan is set up and tested on a phantom representing the patient. One desired part of that process is to keep track on how the radiation generator is positioned during the treatment and to monitor the dose given in the different positions. This has been provided by ScandiDos AB in their product called Delta$^4$ treatment system, which comprises a radiation detector mounted at the collimator for monitoring the dose that is actually provided to the patient and for comparison with the conditions measured in a pre-treatment operation by means of a phantom. For an accurate monitoring, information about the position of the radiation detector is required. In the Delta$^4$ treatment system the gantry angle is obtained by means of an angle sensor mounted on the gantry. It would be desired to have the full position of the radiation detector, i.e. the gantry angle as well as the collimator angle from a single position detector.

A prior art device for pretreatment using a phantom, which device comprises a radiation detector to measure radiation levels, is disclosed in WO 2011/098891. In this prior art document it is briefly mentioned that the device can include measurement devices, such as inclinometers, gyroscopes, or gyrometers, which are integrated in the phantom or connected to it, and that such a measurement device can be used for determining spatial orientation of the gantry, the collimator, the table or a 2D radiation detector. However, there are no instructions of how the gantry angle and collimator angle are supposed to be measured by means of the measurement device.

SUMMARY OF THE INVENTION

It would be advantageous to obtain an accurate position of the radiation detector as regards the gantry angle as well as the collimator angle.

To better address this concern, in a first aspect of the invention there is presented a position detector arranged to be mounted at a radiation detector of a radiation therapy treatment apparatus, which includes a gantry rotatable about a gantry rotation axis, and a collimator rotatable about a collimator rotation axis. The radiation detector is mounted at the collimator. The position detector comprises an accelerometer device, which comprises at least one accelerometer, and which is arranged to detect at least gravitational acceleration in at least one dimension; a gyro device, which comprises at least one gyro, and which is arranged to detect at least angular velocity in at least one dimension; and a controller connected with the accelerometer device and the gyro device. In common the accelerometer device and the gyro device are arranged to be operative in three dimensions. The controller is arranged to receive first input data from the accelerometer device and second input data from the gyro device, and to determine at least a collimator angle and a gantry angle by means of the first and second input data. The combination of an accelerometer device and a gyro device for a position detector which is to be mounted at the collimator is advantageous and provides for a high angle accuracy in all positions for the gantry angle as well as for the collimator angle. Furthermore, by placing them at the radiation detector they are employable for both pretreatment measurements using a phantom and real-time verification measurements during treatment of a patient. The device disclosed in the above-mentioned WO 2011/09891 is arranged for pretreatment measurements using a phantom, and placing a measurement device in the phantom as suggested therein is naturally of no use for real-time measurements while treating a patient.

According to an embodiment of the position detector, the first input data comprises data related to the gantry angle as measured relative to a reference axis extending at an angle to the gantry axis; wherein the second input data comprises gantry rotation data regarding a direction of gantry rotation about the gantry rotation axis; and wherein the controller is arranged to determine the gantry angle by means of the data related to the gantry angle and the gantry rotation data. A typical accelerometer provides the same data related to the gantry angle at a certain inclination independent of in which direction relative to the reference axis it is inclined. The gantry rotation data from the gyro device facilitates the determination of a correct gantry angle.

According to embodiments of the position detector, the controller is arranged to determine a centrifugal correction of the gantry angle, by means of gravitational acceleration data received from the accelerometer device, or by means of gantry rotation data from the gyro device. Thereby, a high accuracy of the gantry angle is ensured.

According to an embodiment of the position detector, the controller is arranged to determine the collimator angle on basis of at least a start collimator angle; and data regarding collimator rotation about the collimator rotation axis, received from the gyro device. This is an advantageous way of using the gyro device for detection of the collimator angle.

According to the invention there is provided a radiation detector arranged to be mounted at a collimator of a radiation therapy treatment apparatus, and comprising the above-described position detector. It is advantageous to co-mount the position detector with the radiation detector, or even integrate them as a single device.

According to the invention there is provided a radiation therapy treatment apparatus comprising such a radiation detector.

According to another aspect of the present invention there is provided a method of detecting a position at a radiation therapy treatment apparatus, which comprises a gantry rotatable about a gantry rotation axis, and a collimator rotatable about a collimator rotation axis, an accelerometer device arranged to detect at least gravitational acceleration in at least one dimension and being placed at the collimator, and a gyro device arranged to detect at least angular velocity in at least one dimension and being placed at the collimator. In common the accelerometer device and the gyro device are arranged to be operative in three dimensions. The method comprises receiving first input data from the accelerometer device, and second input data from the gyro device; and determining at least a collimator angle and a gantry angle by means of the first and second input data. This method and embodiments thereof provide solutions and advantages corresponding to those provided by the position detector and respective corresponding embodiments thereof.

According to an additional embodiment of the method, it further comprises determining, by means of successive gantry angle data items, whether the gantry angle is increasing or decreasing, and using the result in combination with associated gantry rotation data to determine whether the gantry angle is on one or the other side of the reference axis. This is a reliable way of ensuring that the gantry angle is correctly determined.

According to an additional embodiment of the method the operation of determining at least a collimator angle and a gantry angle comprises determining the collimator angle by:

preparing a start collimator angle at the beginning of a radiation therapy treatment;

receiving, with the second data, collimator rotation data; and determining the collimator angle by means of the start collimator angle and the collimator rotation data.

According to an additional embodiment of the method the operation of preparing a start collimator angle comprises:

receiving, with the first input data, auxiliary collimator angle data;

determining whether the gantry angle is within a predetermined interval for obtaining accurate auxiliary collimator angle data;

if the gantry angle is within the predetermined interval, then determining the collimator angle by means of the auxiliary collimator data;

else recording a change of the collimator angle from the start position by means of subsequent collimator rotation data until the gantry angle is within the predetermined interval, receiving new auxiliary collimator angle data, and determining the start collimator angle by means of the new collimator angle data and the change of collimator angle.

This is an advantageous way of independently providing the controller with a start angle.

According to an additional embodiment of the method, it further comprises receiving collimator angle data from the accelerometer device for adjusting the collimator angle. In case the data from the gyro is drifting the absolute collimator angle can be corrected by means of the collimator angle data from the accelerometer.

BRIEF DESCRIPTION OF THE DRAWINGS

The invention will now be described in more detail and with reference to the appended drawings in which.

DESCRIPTION OF EMBODIMENTS

Figure 1:
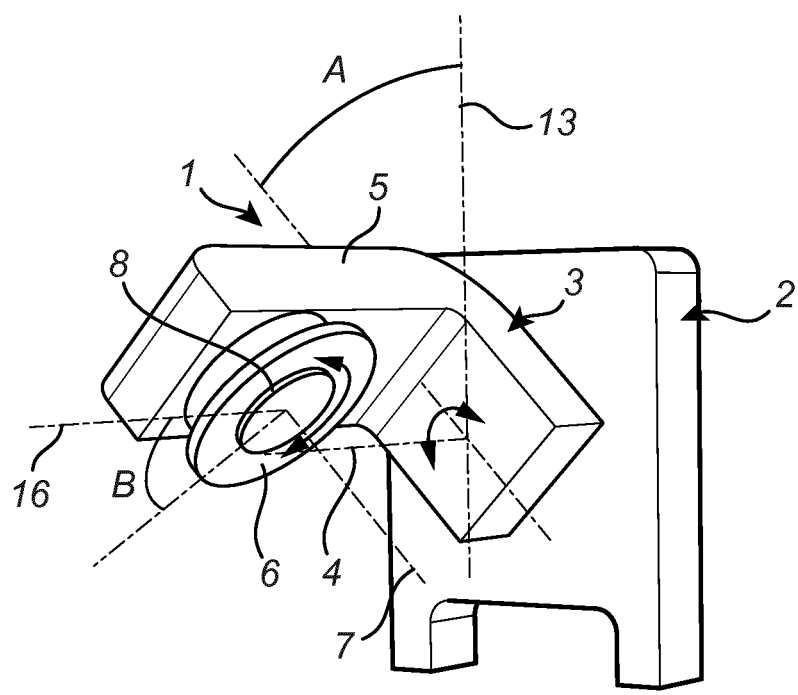
FIG. 1 is a schematic perspective view of a radiation therapy treatment apparatus comprising an embodiment of the position detector according to the present invention.
Figure 2:
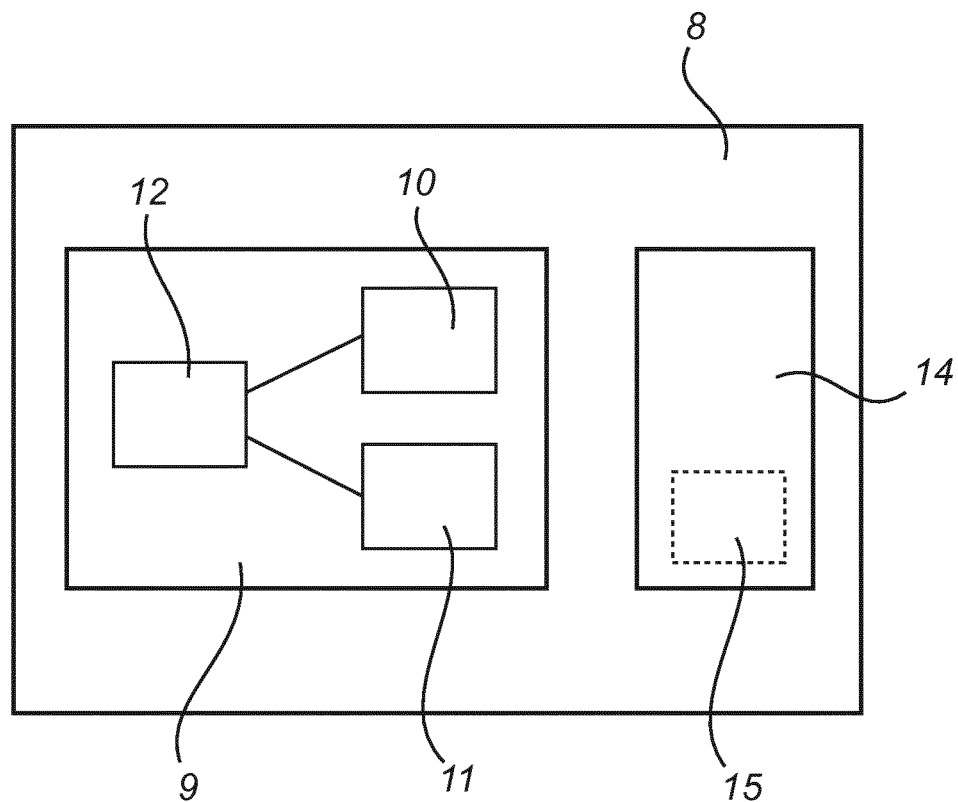
FIG. 2 is a block diagram of a radiation detector comprising the position detector of FIG. 1.

In order to describe embodiments of the position detector, first the environment in which it is arranged to be used will be described, with reference to FIG. 1. Thus, an example of a radiation therapy treatment apparatus 1 comprises base 2, and a gantry 3, rotatably mounted at the base 2, and being rotatable about a gantry rotation axis 4, which in this example is horizontal. The gantry 3 has an arm 5 protruding from the base 2 about in parallel with the gantry rotation axis 4. The radiation therapy treatment apparatus 1 further comprises a collimator 6 rotatably mounted at the end of the arm 5, and being rotatable about a collimator rotation axis 7. According to this example of the radiation therapy treatment apparatus 1, the collimator rotation axis has a fixed position, and it is perpendicular to the gantry rotation axis 4. However, another feasible example is that the collimator rotation axis 7 extends at a fixed but non-perpendicular angle to the gantry rotation axis 4. The most general way of determining gantry angle and collimator angle set forth herein is, however, applicable to all those examples. A radiation detector 8 is mounted at the collimator 6, and comprises a position detector 9, as shown in FIG. 2.

This embodiment of the position detector 9 comprises an accelerometer device 10 comprising a single accelerometer, which is arranged to detect gravitational acceleration in three dimensions, a gyro device comprising a single gyro, i.e. gyroscope, 11 arranged to detect angular velocity in three dimensions, and a controller 12 connected with the accelerometer 10 and the gyro 11. An example of a useful accelerometer, which is provided as an inclinometer, is ADIS16210, manufactured by Analog Devices, which uses a MEMS (Micro-ElectroMechanical Sensor) to detect gravitational acceleration, and is able to output both angle data and acceleration data. Thus, it has internal circuitry for determining the angles from the acceleration values. As an obvious alternative, an accelerometer providing merely the acceleration data can be used, where the determination of the corresponding inclination is done by the controller 12 according to a commonly known formula. Then the output data from the accelerometer does not explicitly represent a value of the inclination, but is still related to the inclination. Consequently, inter alia, the inclinometer 10 is arranged to output data related to the gantry angle, i.e. gantry angle data, which is used for determining a gantry angle A. The gantry angle A is an angle of gantry rotation, and is defined in relation to a reference position, e.g. a reference axis 13 as chosen here for reasons of clarity. According to this embodiment the reference axis 13 is perpendicular to the gantry rotation axis 4 and extends vertically upwards from the gantry rotation axis 4. The gyro 11 detects angular acceleration in three dimensions. Furthermore, the radiation detector 8 comprises radiation detection circuitry 14. The radiation detection circuitry 14 can include a main control unit 15, shown with hatched lines, which communicates with the controller 12 of the position detector, or the controller 12 is the also the main control unit for the whole radiation detector 8. The position detector 9 can be placed within the housing of the radiation detector 8 or within a separate housing but still arranged at the radiation detector 8.

Figure 3:
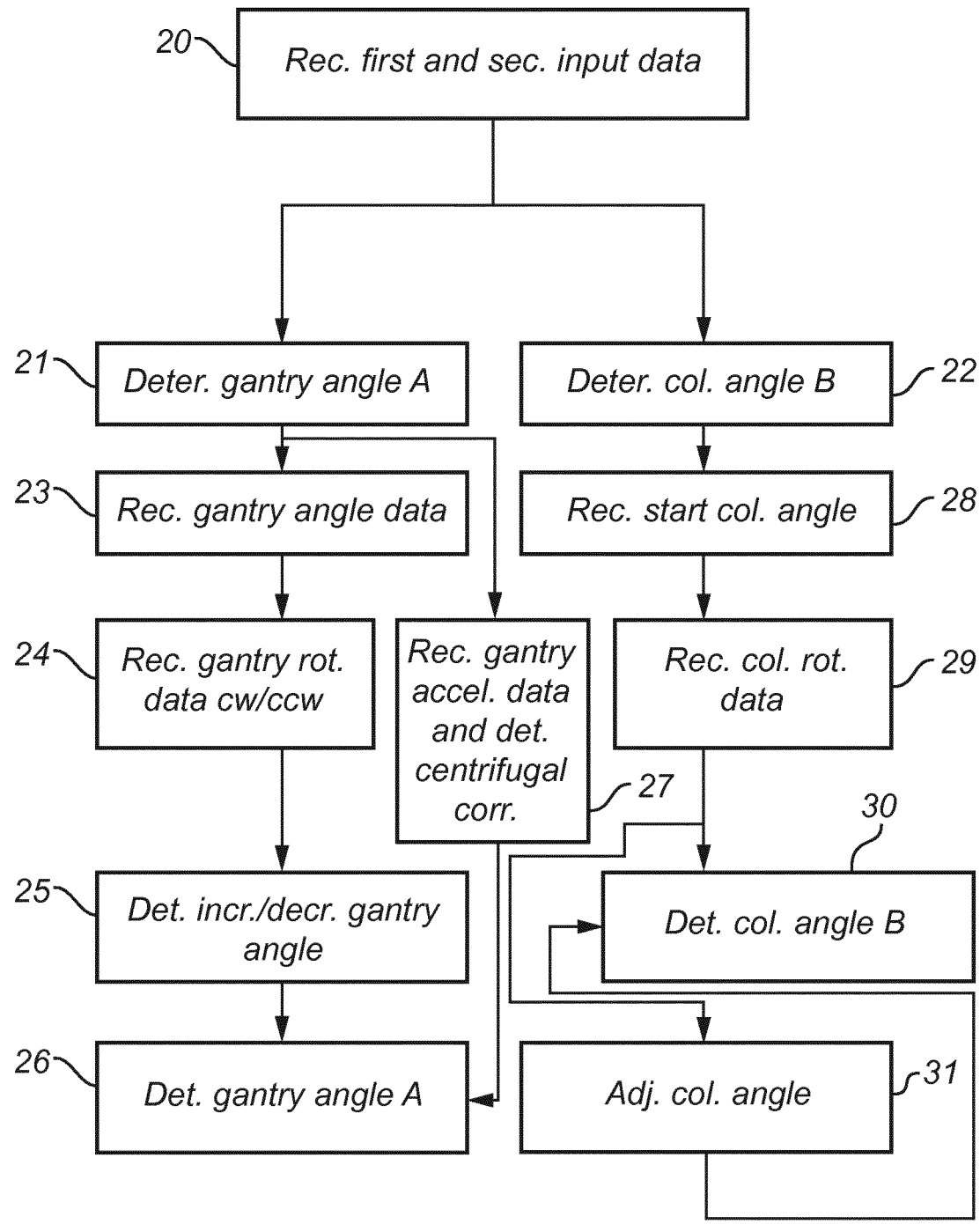
FIG. 3 is a flow chart of an embodiment of the method according to this invention.

The position detector 9 described above operates according to the following embodiment of the present method of detecting a position at a radiation therapy treatment apparatus. The controller 12 receives first input data, representing at least gravitational acceleration in three dimensions, from the accelerometer, i.e. the inclinometer 10, and second input data representing at least angular velocity in three dimensions, from the gyro 11, see box 20 in the flow chart of FIG. 3. The angular velocity is integrated to give the angle together with the start-angle. With the above exemplified inclinometer both the original gravitational acceleration data and the calculated corresponding inclination data is comprised in the first input data. The controller determines the gantry angle A, and a collimator angle B by means of the first and second input data, boxes 21 and 22, respectively. The collimator angle B is an angle of collimator rotation, and is defined e.g. in relation to a reference axis 16 extending radially of the collimator surface from the collimator rotation axis 7 and outwards, in parallel with the arm 5 of the gantry 3.

Figure 4:
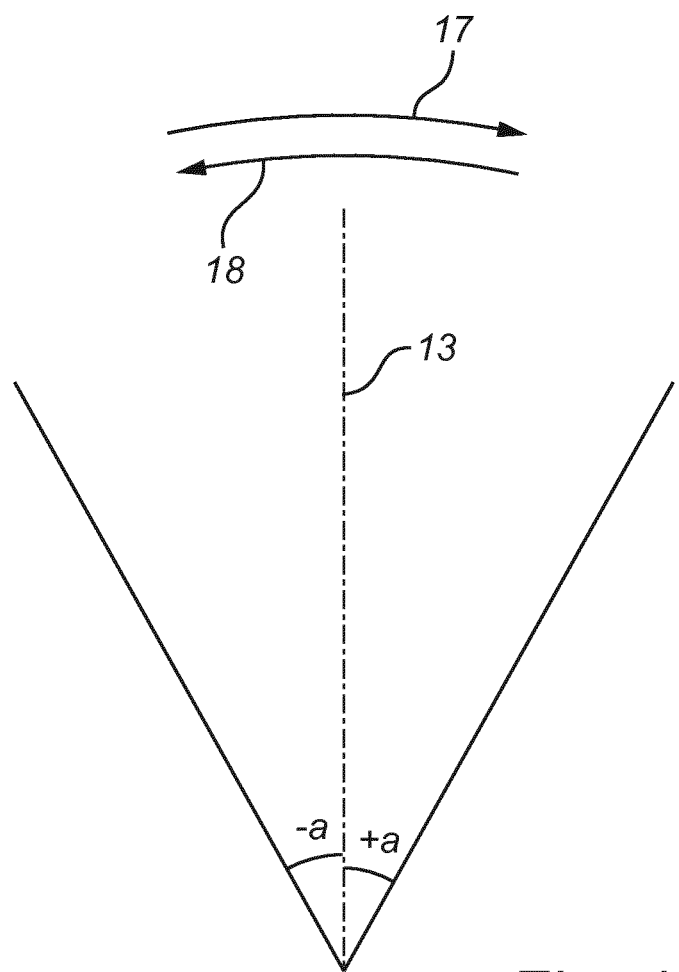
FIG. 4 illustrates gantry angles.

The operation of determining the gantry angle A comprises receiving gantry angle data from the inclinometer 10 regarding an angle relative to the vertical reference axis 13, box 23; and receiving gantry rotation data regarding a direction of gantry rotation about the gantry rotation axis 4 from the gyro 11, box 24. Since the inclinometer 10 and the gyro 11 are operating in three dimensions, they output data related to x, y, and z axes. With a typical mounting of the inclinometer 10, and the gyro 11, the gantry angle and rotation are related to their z axes, while the collimator angle and rotation are related to their x and y axes. The determination of the gantry angle A is primarily done by means of the gantry angle data, e.g. related to the z axis, from the inclinometer 10. Typically, the angle data received from the inclinometer 10 ranges from 0 degrees to 180 degrees. However, the angle data is to be interpreted as an absolute value. In this case it is important whether a detected gantry angle A is +A degrees or −A degrees, see FIG. 4, but +A and −A generates the same angle data A from the inclinometer 10. As mentioned above, the gyro 11 provides gantry rotation data, i.e. data telling whether the gantry is currently moving clockwise (cw) 17, or counter clockwise (ccw) 18 to the controller 12. It is understood that the gantry 3 rotates either continuously or step by step during the treatment. Additionally, the controller 12 determines, by means of successive gantry angle data items related to the z-axis and obtained from the gyro 11, whether the gantry angle is increasing or decreasing, box 25, and this information in combination with the associated gantry rotation data enables the controller 12 to determine if the gantry angle is on one or the other side of the vertical axis 13, i.e. plus or minus the absolute value of the gantry angle data, box 26.

When the gantry 3 rotates it slightly affects the measurement of the gantry angle done by the inclinometer by a centrifugal force, adding an error to the gantry angle data, which makes the gantry angle A slightly inaccurate. In order to compensate for the centrifugal force error, the method further comprises receiving gravitational acceleration data from the inclinometer 10, and using the gravitational acceleration data to determine a centrifugal correction, box 27. By determining a change of the gantry angle $\Delta A$ during a predetermined time period, i.e. by means of two consecutive measurements, or samples, of the gravitational acceleration data, or of the gantry angle data, the controller 12 is able to determine a correction angle $A_{corr}$ as a predetermined constant c times the change of gantry angle $\Delta A$, i.e. $A_{corr}=c\Delta A$. The centrifugal correction is then used by the controller 12 to adjust the gantry angle A with respect to the centrifugal force error when determining the gantry angle A in box 26.

As an alternative to using input from the inclinometer 10, the controller 12 uses input from the gyro 11.

Since the inclinometer 10 might not be mounted in the center of the collimator rotation axis 7 the gantry angle measurement will be affected by centrifugal force from collimator rotation. The correction for this is similar to the correction of the gantry angle described above.

The operation of determining the collimator angle B comprises receiving a start collimator angle at the beginning of a radiation therapy treatment, box 28; receiving collimator rotation data from the gyro 11, box 29; and determining the collimator angle B by means of the start collimator angle and the collimator rotation data, box 30. When starting the treatment, since the gyro senses movement, it is not possible to obtain the collimator angle position from the gyro 11. Either the radiation therapy treatment apparatus 1 is programmed to always return the collimator to a predetermined position at the end of a treatment, and then the controller 12 is programmed to begin calculating the collimator angle B from that position, or the position detector is arranged to determine the start collimator angle itself. In this embodiment of the method, the start collimator angle is received from external input, which input is read from the radiation therapy treatment system by a computer and sent to the position detector 9. As an alternative external input, the start collimator angle can be input by the operator of the therapy treatment apparatus 1. Having above defined the z-axis as related to the gantry angle, subsequent determinations of the collimator angle are done by using angular velocity data related to the x-axis and angular velocity data related to the y-axis from the gyro 11. The present collimator angle is obtained by integrating the angular velocities, determining the corresponding change in collimator angle and adding the change to the preceding collimator angle. The gantry and collimator angles A, B are stored.

During the treatment the operator compares the stored gantry angles A and collimator angles B with corresponding angle data received from the radiation therapy treatment apparatus 1. If there is a difference in any of the angles the cause may have to be examined. In this way the independent angle measurements performed by the position detector 9 are useful for ensuring that the treatment has been executed according to the treatment plan that was prepared in advance.

Since the method is based on using merely the gyro 11 for subsequently determining the collimator angle B, there could arise an error due to drifting sensor values from the gyro 11, which would generate an increasing collimator angle error over time. In order to prevent such a drifting error the method, in this embodiment, further comprises receiving collimator angle data from the inclinometer 10 for adjusting the collimator angle B, box 31. However, when the gantry angle is close to 0 or 180 degrees, and, consequently, the collimator 6 is horizontal or close to horizontal, the inclinometer 10 generates rather inaccurate angle data in the xy plane due to the small gravitational influence on the detector elements in the x and y directions. Therefore, the correction of the collimator angle B is conditional in that the absolute value of the gantry angle preferably should be within the interval of 45 to 135 degrees. This means that the collimator 6, in other words the main plane in which the collimator rotates, is within −45 and +45 degrees relative to its vertical position. Angles outside of this interval are possible but generally provide an undesirably inaccurate value.

Figure 5:
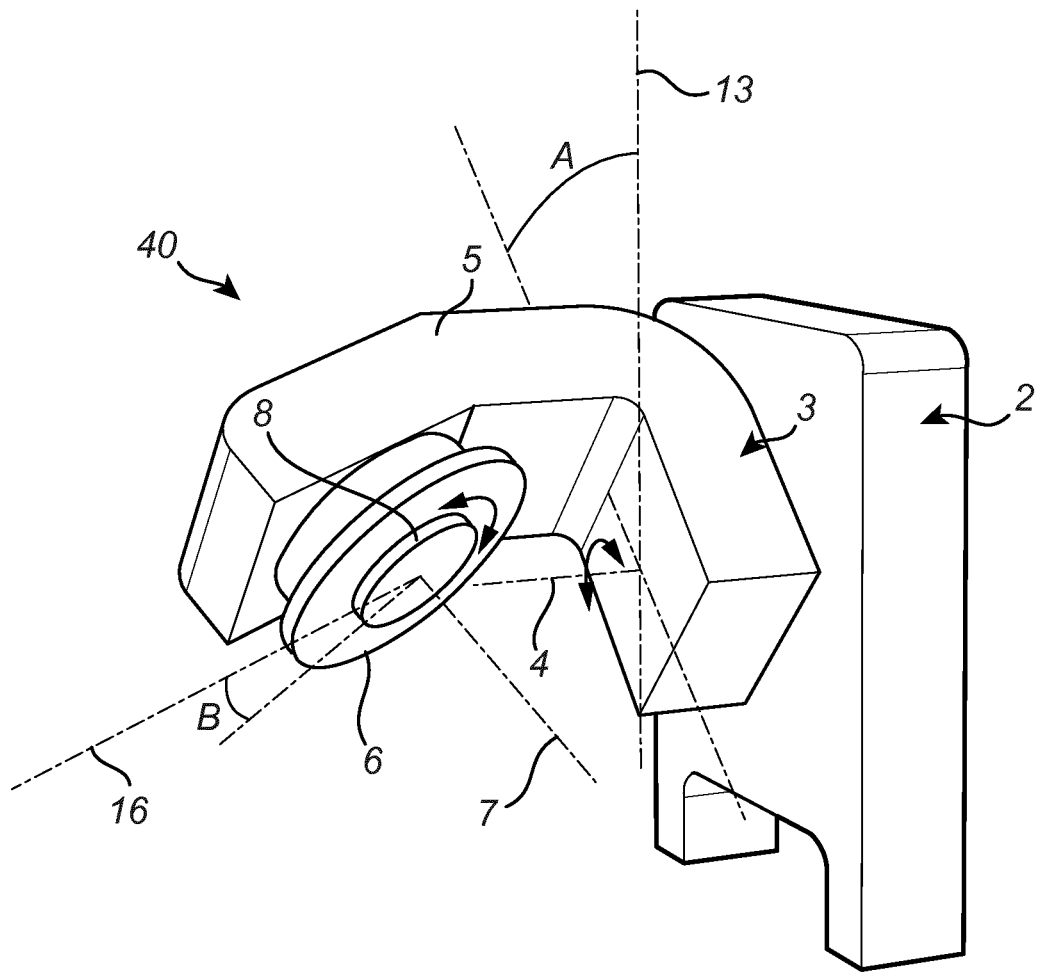
FIG. 5 is a schematic perspective view of another embodiment of a radiation therapy treatment apparatus.

An alternative embodiment of the radiation therapy treatment apparatus 40 is shown in FIG. 5. The same reference numerals as in FIG. 1 have been used for corresponding parts, except for the reference numeral for the whole apparatus. According to this embodiment, the collimator rotation axis 7 extends at a fixed but non-perpendicular angle to the gantry rotation axis 4, the latter still extending horizontally. In this embodiment the determination of the gantry angle A will be affected by a constant error due to the inclination offset of the z axis of the accelerometer device 10. Since this inclination offset is known in advance it is easily compensated for in the determinations of the gantry angle A.

As defined in the claims, the accelerometer device and the gyro device will have to be respectively arranged for detection in at least one dimension, but in combination they will cover all three dimensions. Above, merely three dimensional devices have been described. As an example of an alternative embodiment, the accelerometer device comprises an accelerometer which detects gravitational acceleration in one dimension, which is arranged to be a z axis detector, while the gyro device is arranged to detect angular velocity in three dimensions. In this embodiment, the gantry angle and the collimator angle are determined in the same way as above. However, it is not possible to compensate for a drifting gyro device by means of the accelerometer device.

Further dimensional combinations may be usable as well.

While the invention has been illustrated and described in detail in the drawings and foregoing description, such illustration and description are to be considered illustrative or exemplary and not restrictive. The invention is not limited to the disclosed embodiments.

For example, in further embodiments of the position detector 9 and the method, the start collimator angle B is obtained internally of the position detector 9. When the collimator 6 is in a favourable position at or around its vertical position, i.e. when the absolute value of the gantry angle A is within a predetermined interval where the accelerometer/inclinometer 10 is sufficiently accurate, such as the above-mentioned interval of 45 to 135 degrees, the collimator angle B is determined by means of the angle data from the inclinometer/accelerometer 10. In case the gantry angle A is within the predetermined interval already at the beginning of the treatment, then the start collimator angle B is obtained directly. However if the gantry angle A is without the predetermined interval, then the controller begins determining and storing the change of the collimator angle by means of the gyro as described above. When the gantry enters the predetermined interval of the gantry angle the controller determines the collimator angle by means of the inclinometer/accelerometer and calculates the start collimator angle, and any intermediate collimator angles of interest by means of the stored values of the change of collimator angle. A further possibility of determining the start collimator angle on basis of internal data is to arranged an additional sensor, or several additional sensors, for detecting when the collimator is at a particular position, i.e. the collimator angle has a particular value, such as 0 degrees, 90 degrees or any other appropriate value, which has been determined in advance. For instance, such an additional sensor could be a mercury switch, which is closed at a particular collimator angle.

As another example it should be noted that the position detector is also usable with an apparatus which does not have a radiation detector. It may have another kind of detector than a radiation detector, or no detector at all except for the position detector. The position detector will still be arranged at the collimator, and will provide collimator and gantry angles as described above.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A position detector configured to be mounted at a radiation detector of a radiation therapy treatment apparatus, comprising:
   an accelerometer device comprising at least one accelerometer, wherein the accelerometer device is configured to detect at least gravitational acceleration in at least one dimension and be operative in three dimensions;
   a gyro device comprising at least one gyro, wherein the gyro device is configured to detect at least angular velocity in at least one dimension and be operative in three dimensions; and
   a controller connected with the accelerometer device and the gyro device, wherein the controller is configured to:
      receive first input data from the accelerometer device and second input data from the gyro device,
      determine a collimator angle associated with a collimator that is rotatable about a collimator rotation axis based on the first and second input data, wherein the radiation detector is mounted at the collimator, and
      determine a gantry angle associated with a gantry that is rotatable about a gantry rotation axis based on the first and second input data.

2. The position detector of claim 1, wherein the first input data comprises data related to the gantry angle as measured relative to a reference axis extending at an angle to the gantry rotation axis, the second input data comprises gantry rotation data regarding a direction of gantry rotation about the gantry rotation axis, and the controller is configured to determine the gantry angle based on the data related to the gantry angle and the gantry rotation data.

3. The position detector according to claim 2, wherein the second data comprises data associated with collimator rotation around the collimator rotation axis, and the controller is configured to determine the collimator angle based on at least:
   a start collimator angle; and
   the data associated with the collimator rotation around the collimator rotation axis.

4. The position detector of claim 2, wherein the first input data comprises gravitational acceleration data, and the controller is configured to determine a centrifugal correction of the gantry angle based on the gravitational acceleration data.

5. The position detector of claim 2, wherein the controller is configured to determine a centrifugal correction of the gantry angle based on the gantry rotation data received from the gyro device.

6. The position detector according to claim 1, wherein the second data comprises data associated with collimator rotation around the collimator rotation axis, and the controller is configured to determine the collimator angle based on at least:
a start collimator angle; and
the data associated with the collimator rotation around the collimator rotation axis.

7. A radiation detector configured to be mounted at a collimator of a radiation therapy treatment apparatus and comprising a position detector, wherein the position detector comprises:
an accelerometer device comprising at least one accelerometer, wherein the accelerometer device is configured to detect at least gravitational acceleration in at least one dimension and be operative in three dimensions;
a gyro device comprising at least one gyro, wherein the gyro device is configured to detect at least angular velocity in at least one dimension and be operative in three dimensions; and
a controller connected with the accelerometer device and the gyro device, wherein the controller is configured to:
receive first input data from the accelerometer device and second input data from the gyro device,
determine a collimator angle associated with the collimator that is rotatable about a collimator rotation axis based on the first and second input data, and
determine a gantry angle associated with a gantry that rotatable about a gantry rotation axis based on the first and second input data.

8. The radiation detector of claim 7, wherein the first input data comprises gravitational acceleration data, and the controller is configured to determine a centrifugal correction of the gantry angle based on the gravitational acceleration data.

9. The radiation detector of claim 8, wherein the second data comprises data associated with collimator rotation around a collimator rotation axis, and the controller is configured to determine the collimator angle based on at least:
a start collimator angle; and
the data associated with the collimator rotation around the collimator rotation axis.

10. The radiation detector of claim 7, wherein the radiation detector is comprised in a radiation therapy treatment apparatus.

11. A method of detecting a position at a radiation therapy treatment apparatus comprising a gantry rotatable about a gantry rotation axis, a collimator rotatable about a collimator rotation axis, an accelerometer device being placed at the collimator and configured to detect at least gravitational acceleration in at least one dimension and be operative in three dimensions, and a gyro device being placed at the collimator and configured to detect at least angular velocity in at least one dimension and be operative in three dimensions, the method comprising:
receiving first input data from the accelerometer device and second input data from the gyro device; and
determining at least a collimator angle and a gantry angle based on the first and second input data.

12. The method according to claim 11, wherein determining at least the collimator angle and the gantry angle comprising:
receiving, with the first input data, data related to the gantry angle measured relative to a reference axis extending at an angle to the gantry rotation axis;
receiving, with the second input data, gantry rotation data related to a direction of gantry rotation around the gantry rotation axis; and
determining the gantry angle based on the data related to the gantry angle and the gantry rotation data related to the direction of the gantry rotation around the gantry rotation axis.

13. The method according to claim 12, further comprising:
determining, based on successive gantry angle data items, whether the gantry angle is increasing or decreasing; and
determining whether the gantry angle is on one or the other side of the reference axis based on the determination of whether the gantry angle is increasing or decreasing and the gantry rotation data related to the direction of the gantry rotation around the gantry rotation axis.

14. The method according to claim 13, further comprising adjusting the gantry angle by a centrifugal correction based on one of gravitational acceleration data from the accelerometer device, and angular velocity data from the gyro device.

15. The method according to claim 12, further comprising adjusting the gantry angle by a centrifugal correction based on one of gravitational acceleration data from the accelerometer device, and angular velocity data from the gyro device.

16. The method according to claim 12, wherein determining at least a collimator angle and a gantry angle comprising determining the collimator angle by:
preparing a start collimator angle at the beginning of a radiation therapy treatment;
receiving, with the second input data, collimator rotation data; and
determining the collimator angle based on the start collimator angle and the collimator rotation data.

17. The method according to claim 11, wherein determining at least a collimator angle and a gantry angle comprises:
preparing a start collimator angle at a beginning of a radiation therapy treatment;
receiving, with the second input data, collimator rotation data; and
determining the collimator angle based on the start collimator angle and the collimator rotation data.

18. The method according to claim 17, wherein preparing a start collimator angle comprises:
receiving, with the first input data, first auxiliary collimator angle data;
determining whether the gantry angle is within a predetermined interval;
in response to a determination that the gantry angle is within the predetermined interval, determining the collimator angle based on the first auxiliary collimator angle data; and
in response to a determination that the gantry angle is not within the predetermined interval, recording a change of the collimator angle from a start position based on subsequent collimator rotation data until the gantry angle is within the predetermined interval, receiving second auxiliary collimator angle data, and determining the start collimator angle based on the second auxiliary collimator angle data and the change of the collimator angle.

19. The method according to claim 18, further comprising receiving collimator angle data from the accelerometer device for adjusting the collimator angle.

20. The method according to claim 17, further comprising receiving collimator angle data from the accelerometer device for adjusting the collimator angle.

* * * * *